United States Patent
Slany et al.

(10) Patent No.: US 6,844,463 B2
(45) Date of Patent: Jan. 18, 2005

(54) METHOD FOR THE CARBONYLATION OF PENTENOIC ACID AND ITS DERIVATIVES THEREOF

(75) Inventors: Michael Slany, Kirchheim (DE); Martin Schäfer, Grünstadt (DE); Michael Röper, Wachenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/433,034

(22) PCT Filed: Dec. 3, 2001

(86) PCT No.: PCT/EP01/14078

§ 371 (c)(1),
(2), (4) Date: May 29, 2003

(87) PCT Pub. No.: WO02/46143

PCT Pub. Date: Jun. 13, 2002

(65) Prior Publication Data

US 2004/0110989 A1 Jun. 10, 2004

(30) Foreign Application Priority Data

Dec. 4, 2000 (DE) .......................... 100 60 313

(51) Int. Cl.$^7$ ........................ C07C 255/00; C07C 69/34; C07C 57/02
(52) U.S. Cl. ........................ 558/357; 560/201; 562/595
(58) Field of Search ................ 558/357; 560/201; 562/595

(56) References Cited

U.S. PATENT DOCUMENTS

| 4,257,973 | A |   | 3/1981 | Mrowca |
| 4,508,660 | A |   | 4/1985 | Sieja |
| 4,933,483 | A |   | 6/1990 | Burke et al. |
| 5,312,979 | A |   | 5/1994 | Denis et al. |
| 2002/0045748 | A1 | * | 4/2002 | Drent et al. ........... 540/485 |
| 2003/0105348 | A1 | * | 6/2003 | Bunel et al. ........... 558/357 |

FOREIGN PATENT DOCUMENTS

| DE | 25 41 640 | 3/1977 |
| EP | 373 579 | 6/1990 |
| EP | 450 577 | 10/1991 |
| EP | 577 204 | 1/1994 |
| EP | 662 467 | 7/1995 |
| GB | 1 497 046 | 1/1978 |
| WO | 98/42717 | 10/1998 |
| WO | 00/14055 | 3/2000 |
| WO | 00/56695 | 9/2000 |

OTHER PUBLICATIONS

XP-002198096 1998.

* cited by examiner

*Primary Examiner*—Paul A. Zucker
(74) *Attorney, Agent, or Firm*—Keil & Weinkauf

(57) ABSTRACT

Process for the carbonylation of n-pentenoic acid or its derivatives of the formula (I)

$$C_4H_7\text{—}R^1 \qquad (I)$$

where $R^1$ is —CN or $COOR^2$ where $R^2$ is hydrogen, alkyl or aryl by reaction of a compound of the formula (I) with carbon monoxide and a compound (II) containing a hydroxyl group in the presence of a catalyst system, wherein the catalyst system is obtainable by reaction of a) a source for a metal ion of a metal (III) of the 8th subgroup of the Periodic Table of the Elements with
b) a bidentate phosphine ligand of the formula (IV)

$$(R^3R^4R^5C)(R^6R^7R^8C)P\text{-}L^1\text{-}X\text{-}L^2\text{-}P(CR^9R^{10}R^{11})(CR^{12}R^{13}R^{14}) \qquad (IV)$$

where $R^3$, $R^4$, $R^5$, $R^6$, $R^7$, $R^8$, $R^9$, $R^{10}$, $R^{11}$, $R^{12}$, $R^{13}$, $R^{14}$ independently of one another is an organic radical which in each case contains a carbon atom, via which the respective radical is linked to the relevant tertiary carbon atom mentioned in formula (IV);

$L^1$, $L^2$ independently of one another are a lower alkylene group;

X is an arylene group.

12 Claims, No Drawings

METHOD FOR THE CARBONYLATION OF PENTENOIC ACID AND ITS DERIVATIVES THEREOF

The present invention relates to a process for the carbonylation of n-pentenoic acid or its derivatives of the formula (I)

$$C_4H_7\text{—}R^1 \quad (I)$$

where $R^1$ is —CN or $COOR^2$ where $R^2$ is hydrogen, alkyl or aryl
by reaction of a compound of the formula (I) with carbon monoxide and a compound (II) containing a hydroxyl group in the presence of a catalyst system, wherein the catalyst system is obtainable by reaction of
a) a source for a metal ion of a metal (III) of the 8th subgroup of the Periodic Table of the Elements with
b) a bidentate phosphine ligand of the formula (IV)

$$(R^3R^4R^5C)(R^6R^7R^8C)P\text{-}L^1\text{-}X\text{-}L^2\text{-}P(CR^9R^{10}R^{11})(CR^{12}R^{13}R^{14}) \quad (IV)$$

where
$R^3$, $R^4$, $R^5$, $R^6$, $R^7$, $R^8$, $R^9$, $R^{10}$, $R^{11}$, $R^{12}$, $R^{13}$, $R^{14}$ independently of one another is an organic radical which in each case contains a carbon atom, via which the respective radical is linked to the relevant tertiary carbon atom mentioned in formula (IV);
$L^1$, $L^2$ independently of one another are a lower alkylene group;
X is an arylene group.

Processes for the carbonylation of n-pentenoic acid or its derivatives of the formula (I) is [sic] known, for example from GB-1497046, DE-A-2541640, U.S. Pat. No. 4,508,660, EP-A-373579, U.S. Pat. No. 4,933,483, EP-A-450577, U.S. Pat. No. 4,257,973, WO 2000/14055, EP-A-577204, WO 2000/56695, EP-A-662467 or WO 2000/42717.

In the processes mentioned, straight-chain or branched products are obtained.

The straight-chain products of the carbonylation of compounds of the formula (I), i.e. adipic acid or its derivatives, are used to a large extent in the preparation of industrially important polymers, in particular polyamides, while the branched products have no importance or only a quantitatively minor importance.

A high n/i ratio with a simultaneously high yield is therefore desirable. The n/i ratio is understood as meaning the ratio of the selectivity of straight-chain products to the selectivity of the branched products. The linearity mentioned in this connection in the prior art designates the selectivity of the straight-chain products. The n/i ratio is calculated from the linearity according to the equation n/i ratio=linearity [%]/(100%)–linearity [%]

With a simultaneously high yield, the n/i ratio in the processes mentioned is unsatisfactory.

Thus according to U.S. Pat. No. 4,933,483, example 6, an n/i ratio of 24 (linearity 96%) is achieved with a yield of only 70%.

WO 98/42717 discloses a yield of 84% (conversion 100%, selectivity 84%) in example 7; however the n/i ratio is only 5.25 (84% of linear product, remainder 16% of branched product).

The present invention is based on the object of making available a process for the carbonylation of n-pentenoic acid or its derivatives of the formula (I) which avoids the disadvantages mentioned in a technically simple and economic manner.

Accordingly, the process defined at the outset has been found.

According to the invention, n-pentenoic acid or its derivatives of the formula (I)

$$C_4H_7\text{—}R^1 \quad (I)$$

are employed, where for the purposes of the present invention mixtures of such compounds are also understood hereunder.

A suitable radical $R^1$ is —CN or $COOR^2$, where $R^2$ can be hydrogen, alkyl or aryl, advantageously hydrogen or alkyl, preferably hydrogen, methyl, ethyl, n-propyl, i-propyl, n-butyl, i-butyl, s-butyl, t-butyl, in particular hydrogen, methyl, ethyl, particularly preferably hydrogen or methyl.

If $R^2$ is an alkyl or aryl group, this can carry substituents, such as functional groups or further alkyl or aryl groups. Preferably, in the case of an alkyl or aryl group, $R^2$ carries no substituents.

A suitable n-pentenoic acid or its derivatives of the formula (I) are basically all isomers, such as cis-2-, trans-2-, cis-3-, trans-3- and 4-isomer, and their mixtures. Such mixtures can contain the same or different radicals $R^1$. Those mixtures are preferred which contain the same radical $R^1$.

Advantageously, the use of cis-2-, trans-2-, cis-3-, trans-3- or 4-pentenenitrile and their mixtures is suitable. Those mixtures are preferred here which contain at least 80% by weight of 3-pentenenitrile, i.e. the sum of cis-3-pentenenitrile and trans-3-pentenenitrile.

In a further advantageous embodiment, the use of cis-2-, trans-2-, cis-3-, trans-3- or 4-pentenoic acid and their mixtures is suitable. Those mixtures are preferred here which contain at least 80% by weight of 3-pentenoic acid, i.e. the sum of cis-3-pentenoic acid and trans-3-pentenoic acid.

In a further advantageous embodiment, the use of methyl cis-2-, trans-2-, cis-3-, trans-3- or 4-pentenoate and their mixtures is suitable. Those mixtures are preferred here which contain at least 80% by weight of methyl 3-pentenoate, i.e. the sum of methyl cis-3-pentenoate and methyl trans-3-pentenoate.

Pentenoic acid and its derivatives as in formula (I) can be obtained according to processes known per se, for example by addition of carbon monoxide and a compound containing a hydroxyl group or of hydrogen cyanide to butadiene in the presence of a catalyst.

According to the invention, compound [sic] of the formula (I) is reacted with carbon monoxide. In this process, carbon monoxide can be employed as a pure compound or in the presence of gases which essentially do not influence disadvantageously the process according to the invention, in particular behave. Suitable inert substances of this type are, for example, nitrogen, hydrogen, carbon dioxide, methane and the rare gases, such as argon.

Advantageously, the molar ratio of compound (I) to carbon monoxide can be at least 1:1, preferably at least 3:1, in particular at least 5:1, preferably in the range from 5:1 to 50:1, particularly preferably in the range from 7:1 to 15:1. If the process according to the invention is carried out at molar ratios of compound (I) to carbon monoxide of less than 5:1, in particular less than 3:1, especially less than 1:1, this may lead to a rapid worsening of the properties of the catalyst system.

According to the invention, compound of the formula (I) is reacted with a compound (II) containing a hydroxyl group. For the purposes of the present invention, compound (II) is understood as meaning individual compounds (II) and mixtures of various compounds of this type.

The nature of compound (II) at least partially determines the final product of the present process. If water is employed as compound (II), the corresponding acid is obtained, whereas when using an alcohol, such as an alkanol, the corresponding ester is obtained. Suitable alcohol is primary, secondary or tertiary, preferably primary, alcohols, advantageously $C_1$–$C_{30}$-alkanols, which can optionally carry substituents, such as one or more halogen, nitrile, carbonyl, alkoxy or aryl groups. Advantageously, suitable alkanol is methanol, ethanol, n-propanol, i-propanol, n-butanol, i-butanol, s-butanol, t-butanol, n-hexanol, n-octanol, i-octanol, 2-ethylhexanol, cyclohexanol, benzyl alcohol, phenylethyl alcohol, ethylene glycol, 1,2-propanediol, 1,3-propanediol, neopentyl glycol, trimethylolpropane, pentaerythriol [sic], preferably methanol, ethanol, n-propanol, i-propanol, n-butanol, i-butanol, s-butanol, t-butanol, particularly preferably methanol or ethanol, in particular methanol.

The molar ratio of compound (I) to compound (II) is not critical per se and can lie in a wide range, advantageously in the range from 0.001:1 to 100:1 mol/mol.

The process according to the invention is carried out in the presence of a catalyst system which is obtainable by reaction of a source of a metal ion of a metal (III) with a bidentate phosphine ligand of the formula (IV).

Suitable metal (III) is a metal of the 8th subgroup of the Periodic Table, such as iron, cobalt, nickel, ruthenium, rhodium, palladium, osmium, iridium, platinum, preferably palladium, platinum, rhodium, iridium, in particular palladium, and their mixtures.

The source of a metal ion of such a metal can advantageously be salts of such metals with, or compounds in which such a metal is weakly coordinatively bonded to, an anion which is derived from mineral acids, such as nitric acid, sulfuric acid, phosphoric acid, carboxylic acids, advantageously $C_1$–$C_{12}$-carboxylic acid, preferably acetic acid, propionic acid, butyric acid, sulfonic acid, such as methanesulfonic acid, chlorosulfonic acid, fluorosulfonic acid, trifluoromethanesulfonic acid, benzenesulfonic acid, naphthalenesulfonic acid, toluenesulfonic acid, in particular p-toluenesulfonic acid, t-butylsulfonic acid, 2-hydroxypropanesulfonic acid, sulfonated ion exchangers, haloperacids, such as perchloric acid, perfluorinated carboxylic acids, such as trifluoroacetic acid, nonafluorobutanesulfonic acid, trichloroacetic acid, phosphonic acids, such as benzenephosphonic acid, acids which are derived from the interaction of Lewis acids with Broensted acids, anions, such as tetraphenylborate and derivatives thereof, or their mixtures.

Likewise, compounds can advantageously be employed in which such a metal is present in zero valent form with readily removable ligands, such as, for example, tris(dibenzylideneacetone)-palladium, tetrakis(triphenylphosphane)palladium, bis(tri-o-tolylphosphane)palladium.

The molar ratio of metal (III) to compound (I) is not critical per se. A molar ratio of metal (III) to compound (I) in the range from $10^{-7}$:1 to $10^{-1}$:1, preferably $10^{-6}$:1 to $10^{-2}$:1, has proven advantageous.

According to the invention, the compound (IV) employed is a bidentate phosphine ligand of the formula

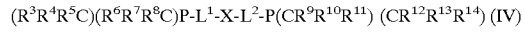

$(R^3R^4R^5C)(R^6R^7R^8C)P-L^1-X-L^2-P(CR^9R^{10}R^{11})(CR^{12}R^{13}R^{14})$ (IV)

where $R^3$, $R^4$, $R^5$, $R^6$, $R^7$, $R^8$, $R^9$, $R^{10}$, $R^{11}$, $R^{12}$, $R^{13}$, $R^{14}$ independently of one another is an organic radical which in each case contains a carbon atom, via which the respective radical is linked to the relevant tertiary carbon atom mentioned in formula (IV);

$L^1$, $L^2$ independently of one another are a lower alkylene group;

X is an arylene group.

The radicals $R^3$, $R^4$, $R^5$, $R^6$, $R^7$, $R^8$, $R^9$, $R^{10}$, $R^{11}$, $R^{12}$, $R^{13}$, $R^{14}$ can independently of one another be chosen in a wide range of organic groups. Preferred organic groups are lower alkyl groups, preferably linear or branched $C_1$–$C_4$-alkyl groups, such as methyl, ethyl, n-propyl, i-propyl, n-butyl, i-butyl, s-butyl, t-butyl.

Particularly preferred groups $R^3$, $R^4$, $R^5$, $R^6$, $R^7$, $R^8$, $R^9$, $R^{10}$, $R^{11}$, $R^{12}$, $R^{13}$, $R^{14}$ are those which, together with the tertiary carbon atom to which they are directly linked, form a group which in each case has at least one steric space requirement, such as t-butyl. For the purposes of the present invention, the steric space requirement is understood as meaning the term of "steric hindrance", discussed in: Homogeneous Transition Metal Catalysis—A Gentle Art", by C Masters, published by Chapman and Hall, 1981, page 14 ff.

The groups $L^1$ and $L^2$ can independently of one another be a lower alkylene group, preferably $C_1$–$C_4$-alkylene group, such as methylene, ethylene, n-propylene, n-butylene group, which can be substituted or unsubstituted. $L^1$ and $L^2$ are particularly preferably in each case a methylene group.

Suitable as X is an arylene group, for example a phenylene group, which can be substituted or unsubstituted. Particularly preferred arylene groups here are those in which $L^1$ and $L^2$ are linked to X via adjacent carbon atoms. In the case of a substitution on X, suitable substituents are alkyl groups, in particular $C_1$–$C_4$-alkyl groups, such as methyl, ethyl, n-propyl, i-propyl, n-butyl, i-butyl, s-butyl, t-butyl, alkoxy, carbalkoxy, halogen, nitro, trihalomethyl or cyano groups. Furthermore, X can be a constituent of a saturated or unsaturated polycyclic system, such as naphthalene, tetralin, biphenylene, indene.

Advantageously, the compound (IV) employed can be bis(di-t-butylphosphino)-o-xylene ("1,2-bis(di-t-phosphino)-benzene"), bis(di-t-neopentylphosphino)-o-xylene and 1,2-bis(di-t-phosphino)naphthalene.

Furthermore, suitable compound (IV) are those bidentate phosphines which are bonded to polymers, preferably via the group X, $L^1$ or $L^2$. Thus, for example, bis(di-t-butylphosphino)-o-xylene can be bonded to polystyrene via the o-xylene group. In such a case, a heterogeneous catalyst system is obtained.

The molar ratio of ligand (IV) to metal (III) can be chosen in a wide range. Advantageously, a ratio in the range from 0.5 to 50, preferably 0.5 to 20, particularly preferably 0.5 to 10, in particular 1 to 5 mol/mol, is suitable.

In a preferred embodiment, the catalyst system is obtainable in the presence of an anion source (V).

The anion source employed can be compounds which already contain the anion, such as salts, or compounds which can release an anion by chemical reaction, such as heterolytic bond cleavage, employed [sic].

Suitable anion sources are known, for example, from EP-A-495 547.

The anion source (V) can advantageously be compounds which are able, with removal of an $H^+$ ion, to make available an anion, such as nitric acid, sulfuric acid, phosphoric acid, carboxylic acids, advantageously $C_1$–$C_{20}$-carboxylic acid, preferably acetic acid, propionic acid, 2,4,6-trimethylbenzoic acid, 2,6-dichlorobenzoic acid, 9-anthracenecarboxylic acid, pivalic acid, 1,2,3-benzenetricarboxylic acid, 1,2,3-benzenetricarboxylic acid-1,3-diester, 2-ethoxy-1-naphthalenecarboxylic acid, 2,6- dimethoxybenzoic acid, 5-cyanovaleric acid, sulfonic acid, such as methanesulfonic acid, chlorosulfonic acid, fluorosulfonic acid, trifluoromethanesulfonic acid, benzenesulfonic acid, naphthalenesulfonic acid, toluenesulfonic acid, in particular p-toluenesulfonic acid, t-butylsulfonic acid, 2-hydroxypropanesulfonic acid, sulfonated ion exchangers, haloperacids, such as perchloric acid, perfluorinated carboxylic acids, such as trifluoroacetic acid, nonafluorobutanesulfonic acid, trichloroacetic acid, phosphonic acids, such as benzenephosphonic acid, acids which are derived from the reaction of Lewis acids, such as $BF_3$, $PF_5$, $AsF_5$, $SbF_5$, $TaF_5$ or $NbF_5$, with a Broensted acid, such as HF (for example fluorosilicic acid, $HBF_4$, $HPF_6$, $HSbF_6$, tetraphenylboric acid and derivatives thereof) or their mixtures.

Among the compounds (V) which are able, with removal of an H+ ion, to make available an anion, those are preferred which have a $pk_a$ of at most 3.5, in particular at most 2.

The molar ratio of compound (V) to metal (III) is not critical per se. Advantageously, the molar ratio of compound (V) to metal (III) can lie in the range from 0.5 to 100, preferably 1 to 20 mol/mol.

The catalyst system can be prepared before use in the process according to the invention or in the process according to the invention itself.

If the catalyst system is prepared in the process according to the invention itself, the use has proven advantageous of those compounds of metal (III) which are soluble in the reaction mixture to the extent that they can form an active catalyst system with the other components.

The catalyst system employed in the process according to the invention can be employed in homogeneous or heterogeneous, preferably homogeneous, phase.

The catalyst system can advantageously be obtained in liquid phase. The liquid phase can in this case be formed by one or more of the components from which the catalyst system is obtainable or was obtained. Likewise, it is possible to prepare the liquid phase by means of an inorganic or organic, preferably organic, liquid diluent.

Suitable liquid diluent is advantageously aprotic liquid diluents, such as ethers, for example diethyl ether, dimethyl ether, dimethyl ether of ethylene glycol, dimetyhl [sic] ether of diethylene glycol, tetrahydrofuran, polyethers, functionalized polyethers, anisole, 2,5,8-trioxanonane, diisopropyl ether, diphenyl ether, such as aromatics, including halogenated aromatics, for example benzene, toluene, o-xylene, m-xylene, p-xylene, chlorobenzene, o-dichlorobenzene, m-dichlorobenzene, p-dichlorobenzene, such as alkanes, including halogenated alkanes, for example hexane, heptane, 2,2,3-trimethylpentane, methylene dichloride, tetrachloromethane, such as nitriles, for example benzonitrile, acetonitrile, such as esters, for example methyl benzoate, methyl acetate, dimethyl phthalate, butyrolactone, such as sulfones, for example diethyl sulfone, diisopropyl sulfone, tetrahydrothiophene 1,1-dioxide ("sulfolane"), 2-methylsulfolane, 3-methylsulfolane, 2-methyl-4-butylsulfolane, such as sulfoxides, for example dimethyl sulfoxide, such as amides, including halogenated amides, for example dimethylformamide, dimethylacetamide, N-methylpyrrolidone, such as ketones, for example acetone, methyl ethyl ketone, methyl isobutyl ketone, and their mixtures.

Particularly preferred liquid diluents are those whose boiling point is higher than the boiling point of the respective product obtained by the process according to the invention. By this means the removal of the product from the remaining reaction mixture, for example by distillation, can be facilitated.

The process according to the invention can advantageously be carried out at a temperature in the range from 20 to 250° C., preferably 40 to 200° C., particularly preferably 70 to 170° C., in particular 80 to 140° C.

The process according to the invention can advantageously be carried out at a total pressure of $1 \times 10^5$ to $200 \times 10^5$ Pa, preferably $5 \times 10^5$ to $70 \times 10^5$ Pa, in particular $6 \times 10^5$ to $20 \times 10^5$ Pa.

The process according to the invention can be carried out continuously, batchwise or semicontinuously.

The process product can be separated from the other components by processes known per se, such as extraction or distillation.

As a result of the high n/i ratio of the process according to the invention, the subsequent purification expenditure is markedly reduced, since fewer undesired by-products are obtained.

A further advantage of the process according to the invention consists in the fact that the residual components which contain the catalyst system can be fed back into the process according to the invention. At the same time, if desired, new catalyst can be added.

EXAMPLES

Example 1

70 mg (0.31 mmol) of palladium acetate, 244 mg (0.62 mmol) of bis(di-t-butylphosphino)-o-xylene ("ligand 1"), 590 mg (3.1 mmol) of p-toluenesulfonic acid, 80 mol (830 mmol) of 3-pentenenitrile ("3-PN") and 34 ml of methanol were filled into a 400 ml glass autoclave having an aerating stirrer, after sealing carbon monoxide was injected up to a pressure of $4 \times 10^5$ Pa and the autoclave was heated to 90° C. In the course of this, the total pressure was adjusted to $7 \times 10^5$ Pa. After the reaction time as in table 1, the autoclave was cooled and the reaction mixture was analyzed by gas chromatography. The result can be seen from table 1.

Example 2

The procedure was as in example 1 with the difference that instead of 3-pentenenitrile 102 ml (840 mmol) of methyl 3-pentenoate ("3-PSE") were employed.

The result can be seen from table 1.

Example 3

The procedure was as in example 1, but instead of palladium acetate and ligand 1 192 mg (0.31 mmol) of palladium acetate-ligand 1 complex were employed.

For the preparation of the palldaium [sic] acetate-ligand 1 complex, 1.0 g (4.4 mmol) of palladium acetate was dissolved in 50 ml of acetone and the solution was filtered through Celite (calcined silica gel). A suspension of 1.73 g (4.4 mmol) in 50 ml of acetone was added to the solution and the mixture was stirred at room temperature for 1 hour. The resulting pale yellow solid was filtered off and dried in vacuo. The yield was 2.57 g (94%).

The result can be seen from table 1.

Example 4

The procedure was as in example 3, but instead of 3-pentenenitrile 102 ml (840 mmol) of methyl 3-pentenoate were employed.

The result can be seen from table 1.

TABLE 1

| Ex | Reaction time [h] | Conversion [%] 3-PN/3-PSE | TOF [h⁻¹] | Carbonylation selectivity [%] | n/i ratio |
|---|---|---|---|---|---|
| 1 | 1 | 90 | 2 400 | >99 | 65.7 |
| 2 | 1 | 92 | 2 500 | >99 | 61.5 |
| 3 | 1 | >99 | 2 650 | >99 | 70.4 |
| 4 | 1 | >99 | 2 700 | >99 | 65.7 |

TOF: (Starting material conversion (3-PN/3-PSE) in moles per hour)/(catalyst amount in moles)

We claim:

1. A process for the carbonylation of n-pentenoic acid or its derivatives of the formula (I)

$$C_4H_7\text{—}R^1 \quad (I)$$

where $R^1$ is —CN or $COOR^2$ where $R^2$ is hydrogen, alkyl or aryl by reaction of a compound of the formula (I) with carbon monoxide and a compound (II) containing a hydroxyl group in the presence of a catalyst system, wherein the catalyst system is obtained by reaction of
a) a source for a metal ion of a metal (III) of the 8th subgroup of the Periodic Table of the Elements with
b) a bidentate phosphine ligand of the formula (IV)

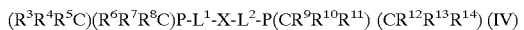

$$(R^3R^4R^5C)(R^6R^7R^8C)P\text{-}L^1\text{-}X\text{-}L^2\text{-}P(CR^9R^{10}R^{11})(CR^{12}R^{13}R^{14}) \quad (IV)$$

where
$R^3$, $R^4$, $R^5$, $R^6$, $R^7$, $R^8$, $R^9$, $R^{10}$, $R^{11}$, $R^{12}$, $R^{13}$, $R^{14}$ independently of one another is an organic radical which in each case contains a carbon atom, via which the respective radical is linked to the relevant tertiary carbon atom shown in formula (IV);
$L^1$, $L^2$ independently of one another are a lower alkylene group;
X is an arylene group.

2. A process as claimed in claim 1, wherein $R^2$ is selected from the group consisting of hydrogen, methyl, ethyl, n-propyl, i-propyl, n-butyl, i-butyl, s-butyl, t-butyl.

3. A process as claimed in claim 1, wherein the compound of the formula (I) employed is to at least 80% by weight 3-pentenenitrile.

4. A process as claimed in claim 1, wherein the compound of the formula (I) employed is to at least 80% by weight methyl 3-pentenoate.

5. A process as claimed in claim 1 metal (III) being selected from the group consisting of palladium, platinum rhodium and iridium.

6. A process as claimed in claim 1, the metal (III) employed being palladium.

7. A process as claimed in claim 1, where $R^3$, $R^4$, $R^5$, $R^6$, $R^7$, $R^8$, $R^9$, $R^{10}$, $R^{11}$, $R^{12}$, $R^{13}$, $R^{14}$, independently of one another in each case are lower alkyl radicals.

8. A process as claimed in claim 1, where the radicals $R^3$, $R^4$, $R^5$, $R^6$, $R^7$, $R^8$, $R^9$, $R^{10}$, $R^{11}$, $R^{12}$, $R^{13}$, $R^{14}$, together with the tertiary carbon atom to which they are directly linked, form a group which in each case has at least one steric space requirement.

9. A process as claimed in claim 1, where $L^1$ and $L^2$ are in each case a methylene group.

10. A process as claimed in claim 1, where the catalyst system is obtainable obtained in the presence of an anion source (V).

11. A process as claimed in claim 10, the anion source (V) employed being a compound which is able, with removal of an H⁺ ion, to make available an anion.

12. The process as claimed in claim 8 wherein said group which has a steric space requirement is t-butyl.

* * * * *

UNITED STATES PATENT AND TRADEMARK OFFICE
CERTIFICATE OF CORRECTION

PATENT NO. : 6,844,463 B2
APPLICATION NO. : 10/433034
DATED : January 18, 2005
INVENTOR(S) : Michael Slany et al.

It is certified that error appears in the above-identified patent and that said Letters Patent is hereby corrected as shown below:

Column 8,
Line 31, "obtainable obtained" should read -- obtained --.

Signed and Sealed this

Twenty-seventh Day of June, 2006

JON W. DUDAS
*Director of the United States Patent and Trademark Office*